United States Patent
Lesso et al.

(10) Patent No.: US 10,237,668 B2
(45) Date of Patent: Mar. 19, 2019

(54) APPARATUS AND METHODS FOR MONITORING A MICROPHONE

(71) Applicant: Cirrus Logic International Semiconductor Ltd., Edinburgh (GB)

(72) Inventors: John Paul Lesso, Edinburgh (GB); Emmanuel Philippe Christian Hardy, Edinburgh (GB)

(73) Assignee: Cirrus Logic, Inc., Austin, TX (US)

( * ) Notice: Subject to any disclaimer, the term of this patent is extended or adjusted under 35 U.S.C. 154(b) by 0 days.

(21) Appl. No.: 15/935,542

(22) Filed: Mar. 26, 2018

(65) Prior Publication Data
US 2018/0288546 A1 Oct. 4, 2018

Related U.S. Application Data (60) Provisional application No. 62/479,077, filed on Mar. 30, 2017.

(30) Foreign Application Priority Data

Apr. 27, 2017 (GB) .................................. 1706704.2

(51) Int. Cl.
*H04R 3/00* (2006.01)
*H04R 29/00* (2006.01)
(Continued)

(52) U.S. Cl.
CPC ........... *H04R 29/004* (2013.01); *G01N 29/42* (2013.01); *G01N 29/4427* (2013.01);
(Continued)

(58) Field of Classification Search
CPC ........ H04R 29/00; H04R 29/004; H04R 3/00; H04R 3/004; H04R 3/005;
(Continued)

(56) References Cited

U.S. PATENT DOCUMENTS

2007/0286441 A1 12/2007 Harsch et al.
2008/0247587 A1 10/2008 Sato
(Continued)

FOREIGN PATENT DOCUMENTS

GB 2497429 A 6/2013
GB 2530565 A 3/2016
(Continued)

OTHER PUBLICATIONS

International Search Report and Written Opinion of the International Searching Authority, International Patent Application No. PCT/GB2018/050752, dated May 16, 2018.
(Continued)

*Primary Examiner* — Thang V Tran
(74) *Attorney, Agent, or Firm* — Jackson Walker L.L.P.

(57) ABSTRACT

This application describes an apparatus (300) for monitoring for blockage of an acoustic (110) port of a microphone device (100). The apparatus has a spectrum peak detect block (301) for receiving a microphone signal ($S_{MIC}$) and determining, from the microphone signal, a resonance frequency ($f_H$) and a quality factor ($Q_H$) of a resonance (202) associated with the acoustic port. A condition monitoring block (302) is configured to determine any change in resonance frequency and quality factor and to determine a blockage status for the microphone based on said detect changes. The condition monitoring block identifies a change in blockage status if there is a change in quality factor.

20 Claims, 5 Drawing Sheets

(51) Int. Cl.
*G01N 29/42* (2006.01)
*G01N 29/44* (2006.01)
*G01N 29/46* (2006.01)
*H04R 19/00* (2006.01)

(52) U.S. Cl.
CPC ............... *G01N 29/46* (2013.01); *H04R 3/00* (2013.01); *H04R 19/005* (2013.01); *H04R 2410/03* (2013.01)

(58) Field of Classification Search
CPC .......... H04R 2201/003; H04R 2410/00; H04R 2410/03; H04R 19/005; H04R 1/265; G01N 29/12; G01N 29/42; G01N 29/46; G01N 29/4427
See application file for complete search history.

(56) References Cited

U.S. PATENT DOCUMENTS

| | | | | |
|---|---|---|---|---|
| 2012/0114157 | A1* | 5/2012 | Arndt | H04R 25/305 381/315 |
| 2012/0250900 | A1 | 10/2012 | Sakai | |
| 2012/0308047 | A1 | 12/2012 | Muza | |
| 2014/0270206 | A1 | 9/2014 | Port | |
| 2015/0214912 | A1 | 7/2015 | Khenkin | |
| 2015/0289073 | A1 | 10/2015 | Salvia et al. | |
| 2015/0304786 | A1* | 10/2015 | Partio | H04R 25/305 381/58 |
| 2016/0050488 | A1* | 2/2016 | Matheja | H04R 3/005 381/56 |
| 2016/0127845 | A1 | 5/2016 | Cagdaser et al. | |
| 2018/0058918 | A1* | 3/2018 | Vitt | G01H 15/00 |

FOREIGN PATENT DOCUMENTS

| | | |
|---|---|---|
| WO | 8402187 A1 | 6/1984 |
| WO | 2016069812 A1 | 5/2016 |

OTHER PUBLICATIONS

International Search Report and Written Opinion of the International Searching Authority, International Patent Application No. PCT/GB2018/050754, dated May 30, 2018.
Yu, Ganghua et al., "Effect of internal resistance of a Helmholtz resonator on acoustic energy reduction in enclosures", The Journal of the Acoustical Society of America, vol. 124, No. 6, Dec. 1, 1008, pp. 3534-3543, NY NY.
International Search Report and Written Opinion of the International Searching Authority, International Patent Application No. PCT/GB2018/050755, dated Jun. 14, 2018.
Combined Search and Examination Report under Sections 17 and 18(3), UKIPO, Application No. GB1706708.3, dated Jun. 15, 2017.
Combined Search and Examination Report under Sections 17 and 18(3), UKIPO, Application No. GB1706707.5, dated Jun. 16, 2017.
Combined Search and Examination Report under Sections 17 and 18(3), UKIPO, Application No. GB1706704.2, dated Jun. 19, 2017.

* cited by examiner

APPARATUS AND METHODS FOR MONITORING A MICROPHONE

This application relates to methods and apparatus for monitoring a microphone, such as a MEMS microphone, and especially to determining operating conditions for the microphone, in particular an acoustic port blockage status and/or temperature information and/or air resonance noise in the signal band.

BACKGROUND

Various electronic devices are provided with microphones, for instance to allow for voice communication, for sound recording and/or for noise cancellation. Voice control is also becoming increasingly popular and to allow for the ability for voice control microphones may be provided on a range of devices. Ultrasonic communication is also of interest for machine-to-machine communication, requiring transducers for the transmitting and/or detecting of a transmitted ultrasonic signal.

MEMS (micro-electromechanical-system) microphones have become increasingly popular, in part because of their small size.

In such applications it is generally desirable to monitor the operating conditions of the microphone, e.g. the MEMS microphone, in order to detect any operating condition(s) that could impact on the performance of the microphone and/or the host device.

SUMMARY

According to one aspect there is provided an apparatus for monitoring for blockage of an acoustic port of a microphone, the apparatus comprising:
 a spectrum peak detect block for receiving a microphone signal and determining, from the microphone signal, a resonance frequency and a quality factor of a resonance associated with the acoustic port,
 a condition monitoring block configured to determine any change in resonance frequency and quality factor with respect to respective reference values of resonance frequency and quality factor and to determine a blockage status for the microphone based on said detect changes.

In some embodiments the apparatus is configured such that, if a change in quality factor with respect to one said reference value of quality factor is determined, the condition monitoring block is configured to output a status signal indicating that there has been a change in blockage status for the acoustic port from a blockage status that corresponds to that reference value of quality factor. The condition monitoring block may be configured such that at least one said reference value of quality factor is based one or more quality factors for the resonance associated with the acoustic port previously determined by the spectrum peak detect block. The apparatus may have a memory for storing a previously determined quality factor or a value derived from a plurality of previously determined quality factors to be used as a reference value of quality factor.

In some embodiments there may be a memory for storing a first reference value of quality factor known to correspond to an unblocked state of the acoustic port. The condition monitoring block may be configured, in use, to compare the determined quality factor to the stored first reference value and to determine that the acoustic port has become at least partly blocked if the determined quality factor is different to the first reference value of quality factor. The first reference value of quality factor may correspond to one of: a quality factor determined in a calibration step; a calculated or modelled quality factor; or a previously determined quality factor for which the condition monitoring block determined that the acoustic port was unblocked.

In some instances, if a change in resonance frequency without a change in quality factor is determined with respect to respective reference values of resonance frequency and quality factor, the condition monitoring block is configured to determine that the blockage status of the acoustic port has not changed.

If a change in resonance frequency without a change in quality factor is determined with respect to respective reference values of resonance frequency and quality factor, the condition monitoring block may be configured to output a status signal indicating that there has been a change in air temperature from a temperature that corresponds to said reference value of resonance frequency. In the event of determining a change in air temperature, the condition monitoring block may be configured to determine an estimate of air temperature based on the determined resonance frequency.

If no change in resonance frequency or quality factor is determined with respect to respective reference values of resonance frequency and quality factor, the condition monitoring block may be configured to output a status signal indicating that there has been no change in operating condition from an operating condition that corresponds to said reference values.

The spectrum peak detect block may comprise a conversion block configured to receive the microphone signal and output a spectrum signal corresponding to a frequency domain version of the microphone signal over at least a predefined frequency range. The conversion block may comprise a Fast Fourier Transform (FFT) block. In which case the spectrum peak detect block may comprise a filter for filtering the output of the FFT block to provide the spectrum signal.

In some instances the spectrum peak detect block may comprise a filter bank configured to receive the microphone signal and output a spectrum signal comprising an indication of the signal amplitude at a plurality or frequencies or frequency bins over at least a predefined frequency range The spectrum peak detect block may comprise a resonance frequency detection block configured to determine the resonance frequency from the spectrum signal. The resonance frequency detection block may be configured to identify the frequency with the highest signal magnitude within the predefined frequency range as the resonance frequency. The resonance frequency detection block may be configured to identify a signal magnitude range between the highest and lowest signal magnitudes within the predefined frequency range, determine a first threshold within the identified signal range and integrate the values of signal magnitude above the first threshold across the predefined frequency range to identify a first frequency at which the integral equal half of the total integral and identify said first frequency as the resonance frequency. The first threshold may be at a signal magnitude corresponding to a level of 50-70% of the signal magnitude range.

The spectrum peak detect block may additionally or alternative comprise a quality factor determination block configured to determine the quality factor from the spectrum signal. The quality factor determination block may be configured to determine a plurality of points associated with the resonance peak in the spectrum signal, to fit a curve to said determined points and to determine an indication of the quality factor from said curve. The quality factor determination block may be configured to determine a first point corresponding to a peak value of signal magnitude, and to identify second a third points a predetermined frequency above and below the first point respectively. The quality factor determination block may be configured to determine the width of the fitted curve at a predetermined magnitude interval below the peak magnitude as the quality factor.

The apparatus may comprise an activity detector configured to determine an indication of activity within the predefined frequency range. The activity detector may be configured to determine an indication of the difference between the current spectrum signal and at least one previous spectrum signal. The spectrum peak detect block may comprise a controller responsive to the activity detector. The controller may be configured such that if the activity is above an activity threshold, the relevant spectrum signal is not used to determine an indication of resonance frequency or quality factor that is output from the spectrum peak detect block.

The apparatus may comprise a noise reduction block configured to process the microphone signal based on at least one characteristic of said resonance associated with the acoustic port of the microphone so as to reduce noise in the processed microphone signal due to said resonance. The at least one characteristic of a resonance associated with the acoustic port of the microphone may comprise at least one of the resonance frequency and quality factor of said resonance determined by the spectrum peak detect block. Additionally or alternatively the at least one characteristic of a resonance associated with the acoustic port of the microphone may comprise a first signal indicative of the relative magnitude of the resonance at a plurality of frequencies or within a plurality of frequency bins determined by the spectrum peak detect block. The noise reduction block may be configured to process the microphone signal according to a first function, wherein said first function is based on said at least one characteristic of a resonance peak. The first function may be determined as an inverse function to the profile of the resonance peak. The noise reduction block may comprise a filter or filter bank.

The apparatus may be implemented as an integrated circuit.

Embodiments also relate to a microphone system comprising a first microphone and an apparatus as described in any of the variants discussed above which is configured to receive a microphone signal from said first microphone.

Aspects also relate to an electronic device comprising an apparatus as described in any of the variants discussed above or the microphone system. The apparatus may be at least one of a: portable device; a battery powered device; a communications device; a mobile or cellular telephone; a smartphone device; a computing device; a laptop, notebook or tablet computer; a gaming device; a wearable device; a voice-controlled or voice activated device.

In a further aspect there is provided a method of monitoring for blockage of an acoustic port of a microphone, the method comprising:
 receiving a microphone signal and determining, from the microphone signal, a resonance frequency and a quality factor of a resonance associated with the acoustic port,
 determining any change in resonance frequency and quality factor with respect to respective reference values of resonance frequency and quality factor; and
 determining a blockage status for the microphone based on any detect changes.

In a further aspect there is an apparatus for monitoring for blockage of an acoustic port of a microphone, the apparatus comprising:
 a spectrum peak detect module configured to analyse a received microphone signal to determine a resonance frequency and a quality factor of a resonance associated with the acoustic port; and
 a condition monitoring block configured to determine a blockage status for the acoustic port of the microphone based on both said determined resonance frequency and said determined quality factor.

The condition monitoring block may be configured to monitor for any change in resonance frequency and also in quality factor and to determine a change in blockage status based on said detected changes.

A further aspect provides an apparatus for monitoring for blockage of an acoustic port of a microphone, the apparatus comprising:
 a quality factor determining block for receiving a microphone signal and determining, from the microphone signal, a quality factor associated of a resonance associated with the acoustic port,
 a condition monitoring block configured determine an blockage status for the acoustic port of the microphone based on said determined quality factor.

In another aspect there is an apparatus for monitoring a microphone device having an acoustic port, the apparatus comprising:
 a spectrum peak detect block for receiving a microphone signal and determining, from the microphone signal, a resonance frequency and a quality factor of a resonance associated with the acoustic port,
 a condition monitoring block configured to determine any change in resonance frequency and quality factor with respect to respective reference values of resonance frequency and quality factor and to determine an operating condition for the microphone based on said detect changes;
 wherein the operating condition comprises at least one of: a blockage status of the acoustic port and an air temperature condition.

There is also provided an apparatus for monitoring an operating temperature condition of a microphone device having an acoustic port, the apparatus comprising:
 a spectrum peak detect block for receiving a microphone signal and determining, from the microphone signal, a resonance frequency and a quality factor of a resonance associated with the acoustic port of the microphone,
 a condition monitoring block configured to determine any change in resonance frequency and quality factor with respect to respective reference values of resonance frequency and quality factor and to determine a temperature condition for the air temperature within the acoustic port based on said determined changes.

There is also provided an apparatus for monitoring an air temperature condition of air within a microphone device, the apparatus comprising:
 a spectrum peak detect module configured to analyse a microphone signal to determine a resonance frequency and a quality factor of a resonance associated with the air within the microphone device; and
 a condition monitoring block configured to determine an air temperature condition for the air within the microphone device based on both said determined resonance frequency and said determined quality factor.

There is also provided a temperature sensor comprising:
 a microphone device;

a spectrum peak detect module for processing a microphone signal produced by the microphone device to identify a Helmholtz resonance peak frequency from the microphone signal; and a temperature estimation module for estimating air temperature based on said determined resonance Helmholtz resonance frequency.

There is also provided a noise reduction apparatus for a microphone device having an acoustic port, the apparatus comprising:

a spectrum peak detect block for receiving a microphone signal and determining, from the microphone signal, at least one characteristic of a resonance peak associated with the acoustic port of the microphone, a noise reduction block configured to process the microphone signal based on said at least one characteristic of a resonance associated with the acoustic port of the microphone so as to reduce noise in the processed microphone signal due to said resonance.

There is also provided a noise reduction circuit for a microphone comprising:

a spectrum peak detect block for processing a microphone signal generated by the microphone to identify at least one characteristic of a spectral peak in the microphone signal due to a Helmholtz resonance; and a noise reduction circuit for processing the microphone signal based on said identified at least one characteristic of the spectral peak to reduce any noise due to the Helmholtz resonance in the processed microphone signal over at least a signal band of interest

BRIEF DESCRIPTION OF THE FIGURES

For a better understanding of the present disclosure, and to show how it may be put into effect, reference will now be made, by way of example only, to the accompanying drawings, in which.

DESCRIPTION

This disclosure relates to monitoring of the operating conditions of a microphone device. Embodiments are particularly applicable to MEMS microphones but the principles are equally applicable to other types of microphone such as electret microphones. The operating conditions may, in some examples, comprise a blockage status of an acoustic port associated with the microphone device. The operating conditions may, in some examples, comprise a temperature condition for air within the microphone device, i.e. information about air temperature, e.g. an estimate of air temperature or information about a change in air temperature. The operating conditions may, in some examples, comprise information about noise due to the air resonance, at least within a signal band of interest, and in some embodiments the microphone signal may be processed to reduce the effect of any identified resonance noise within the signal band of interest, i.e. to improve the signal-to-noise ratio of the microphone signal.

Embodiments of the present disclosure monitor a microphone signal generated by the microphone for a signal component related to a characteristic air resonance associated with the microphone device, i.e. a resonance associated the acoustic path from the outside world to the microphone transducer. The signal component related to such a resonance may be characterised and used to determine information about the operating conditions for the microphone and/or used to reduce or mitigate the noise impact of such resonance.

As will be understood by one skilled in the art a microphone device will comprise a transducer structure having an element that may be deflected by pressure waves, e.g. a flexible membrane, to produce a measurable change in electrical properties. Typically in a microphone device, the transducer structure is enclosed within a protective structure, e.g. a housing or package. To allow pressure waves to reach the transducer structure there will typically be one or more acoustic ports. The microphone device thus comprises a cavity or volume formed within the package or housing and at least one acoustic port for acoustic communication with the external environment. Such a microphone structure will, in use, result in resonance within the cavity/acoustic port which will act upon the transducer structure. Thus the microphone signal produced by the microphone will include a resonance peak associated with this air resonance. The characteristics of the air resonance, and hence the resonance peak in the microphone signal, depend on the dimensions of the relevant air volumes of the microphone device, i.e. the dimensions of the acoustic port and cavity housing the transducer structure. The air resonance will, however, also depend on the air temperature. By detecting and analysing such a resonance peak in the microphone signal it is possible to determine information about any changes in the dimensions of the acoustic port such as may occur when the acoustic port is partly blocked, i.e. occluded. Additionally or alternatively, by detecting and analysing such a resonance peak in the microphone signal it is possible to determine information about air temperature, such as an estimate of air temperature and/or changes in air temperature. Additionally or alternatively characterising the component due to the resonance peak can allow an identification or estimate of any contribution to the microphone signal due to the air resonance in a signal band of interest. Such contribution may be useful for determining an operating condition of the microphone as noted above, but otherwise represents noise in the microphone signal. In some instances the microphone signal may be processed to reduce or eliminate such resonance components and thus improve the SNR (signal-to-noise ratio) of the microphone.

Figure 1:
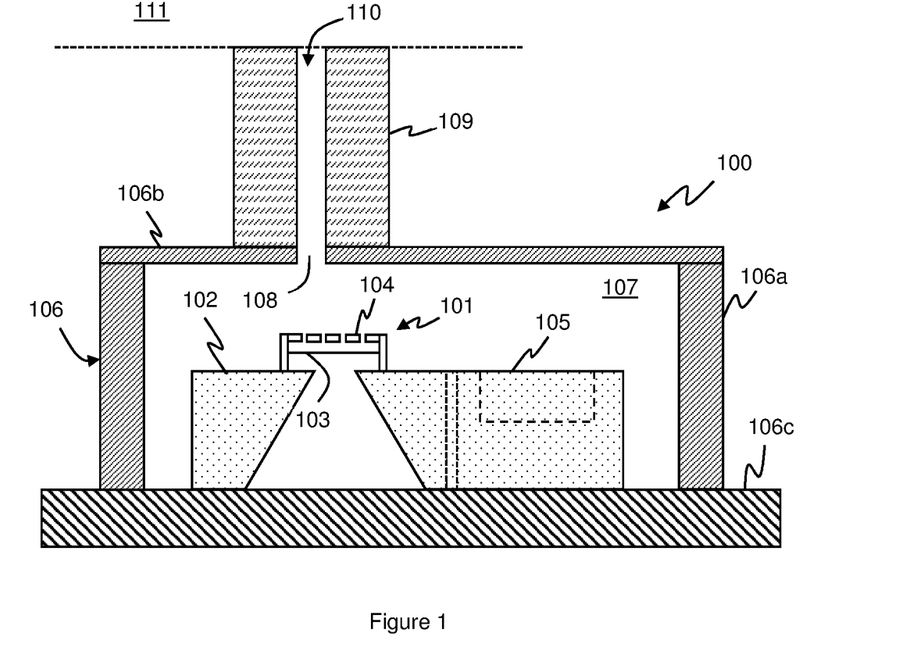
FIG. 1 illustrates a packaged MEMS transducer having an associated acoustic port.

FIG. 1 illustrates one example of a packaged MEMS microphone device 100 having an acoustic port. In this example the microphone package comprises a MEMS microphone transducer 101 formed on a transducer substrate 102. The transducer 101 typically comprises a membrane or diaphragm 103 that may be displaced by an incident pressure wave, e.g. an acoustic stimulus. Note that as used herein the term acoustic shall be used to refer to any type of pressure wave that may propagate through air to deflect the membrane or diaphragm including, but not limited to, pressure waves at frequencies audible to a human, i.e. audible sound. For the avoidance of doubt the term acoustic shall be taken to include signals at ultrasonic frequencies.

The membrane or diaphragm 103 forms or carries a first electrode (not illustrated separately in FIG. 1). The membrane or diaphragm 103 is supported relative to at least one fixed back-plate structure 104 that has a second electrode (also not illustrated separately in FIG. 1). In response to an incident acoustic wave the moveable first electrode of the diaphragm 103 may tend to be displaced with respect to the fixed second electrode of the back-plate 104. By driving, i.e. biasing, the first and second electrodes with suitable voltages a measurement signal corresponding to the incident acoustic wave can be determined by monitoring the change in electrical properties, for example through measuring the change in capacitance due to deflection of the first electrode relative to the fixed second electrode.

The MEMS transducer structure is thus typically coupled to biasing/read-out circuitry 105 and in some embodiments the transducer 101 and biasing/read-out circuitry 105 are formed as an integrated circuit on the same substrate 102, i.e. the transducer 101 and biasing/read-out circuitry 105 are formed on a monolithic die. In other embodiments the biasing/read-out circuitry 105 may be formed on a separate die to the MEMS transducer structure, as indicated by the two vertical dashed lines within substrate 101 representing the edges of the respective dies in such an arrangement.

In either case the transducer 101 and circuitry 105 are typically packaged together within a housing or package 106. The housing may comprise side wall portions 106a, a lid portion 106b and a base portion 106c. In some instances at least some of these portions of the housing, i.e. package, may be formed from continuous material, e.g. the side wall portion 106a and lid portion 106b may be formed from a shaped metal sheet and bonded to the base, i.e. substrate portion 106c. However in some instances the package may comprise separate components joined together to form the housing and may, for instance, be formed at least partly from printed circuit board (PCB) material such as FR4. In some instances part of the transducer die 102 may form part of the housing structure.

The housing 106 thus defines a cavity, or chamber, 107 within which the transducer 101 resides. To allow acoustic waves to reach the transducer 101, the housing 106 has a housing port 108, e.g. a hole or opening, which in this embodiment is illustrated as being in the cover, i.e. lid, of the package. It will be understood by those skilled in the art that the housing port 108 may alternatively be located in the substrate portion 106c or the side wall portion 106a. Thus the housing port 108 may be an opening, somewhere suitable, in the housing 106, although in some examples the housing port 108 may be sealed with some flexible membrane material to provide a substantially acoustically transparent port for transmission of acoustic waves but to provide a barrier, i.e. an environmental barrier, to ingress of moisture, dirt etc. The housing port 108 thus forms at least part of an acoustic port for the transmission of acoustic waves to the transducer 101 within the housing 106.

In some instances, when such a microphone device is included in an assembled host device, the housing port 108 may be coupled to a structure 109, that at least partly defines an acoustic channel or waveguide for propagation of acoustic waves from a desired location, e.g. from the outside 111 of the host device, to cavity 107 within the microphone package 106 via the housing port 108. For instance structure 109 could be a gasket or the like. In such instances the channel 110, defined partly by guide structure 109 and partly by the housing port 108 can be seen as an acoustic port of the microphone device. In some instances however the channel structure 110 may not be needed, for instance if the microphone package is located in a part of the host device that can readily receive acoustic waves of interest, in which case the acoustic port of the microphone may comprise the housing port alone. It will also be understood that other implementations for arranging a packaged microphone to receive acoustic signals of interest, but in general there will be an acoustic port associated with the packaged microphone.

Such an acoustic system of an air volume or cavity 107 in fluid communication with the environment via an acoustic port 110 will exhibit a characteristic resonance, often referred to as the Helmholtz resonance. This resonance is a resonance of the air within the system and thus will be referred to herein as an air resonance. For instance, when air passes over the entrance to the acoustic port 110 a Helmholtz resonance may be produced. In everyday use air may flow past the entrance to the acoustic port 110 due to air currents or wind, acoustic stimuli (e.g. background noise) or movement of the host device through the air etc. Thus, a Helmholtz resonance may be spontaneously generated within the acoustic port 110 at various times. Acoustic signals passing to the transducer via the acoustic port will also excite the Helmholtz resonance which can effectively amplify acoustic noise. The Helmholtz resonance will have a characteristic frequency profile around a resonance frequency (the Helmholtz frequency $f_H$) which is related the dimensions of the acoustic system, e.g. the dimensions of the acoustic port 110 and internal cavity 107 of the microphone housing 106.

In essence the acoustic path from the outside world to the transducer can be modelled as acoustic impedances, inductances and capacitances. In the example illustrated in FIG. 1 there is an acoustic impedance related to coupling of pressure waves from outside 111 the host device to the acoustic port, in series with an acoustic inductance due to the acoustic port 110 itself and a further acoustic impedance related to the interface between the acoustic port 110 and the cavity 107. The cavity 107 also functions as an acoustic capacitance. This acoustic path can be modelled and behaves as a second order resonator.

This resonance will thus result in a characteristic signal that can be detected as an acoustic signal by the microphone transducer 101. The resulting microphone signal from the MEMS transducer may therefore contain a signal component with the characteristic frequency profile associated with this Helmholtz resonance $f_H$.

It should be noted that electrical connections between the various components and from the components within the package 106 to connections outside the package have been omitted from FIG. 1 for clarity, and the various ways in which such connections may be implemented will be understood by those skilled in the art.

Figure 2:
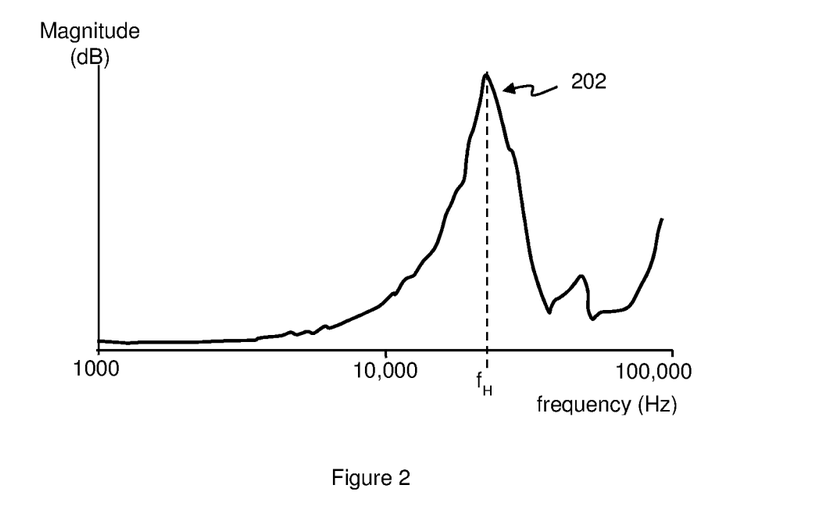
FIG. 2 illustrates an example of a microphone signal from a microphone having an acoustic port.

FIG. 2 illustrates an example of a microphone signal from a packaged microphone having an acoustic port 110, for example for a microphone package such as shown in FIG. 1. Such a signal, recorded in the absence of any specific acoustic stimulus being applied to the microphone, is indicative of the general background signal produced by the microphone. FIG. 2 illustrates a plot of signal magnitude (in dB in this case) against frequency for the microphone signal, i.e. is a spectrogram of the output signal from the microphone output from the readout circuitry 105. It can clearly be seen that a peak 202 occurs in the plot, which in this instance had a peak frequency, i.e. a resonance frequency $f_H$, of around 22 kHz.

This peak 202 in the microphone signal is caused by the resonance associated with the acoustic system, i.e. acoustic port 110 leading to cavity 107 as discussed above. Analysis shows that, for a system such as illustrated in FIG. 1, to first order the peak resonance frequency $f_H$ of this Helmholtz resonance can be estimated as:

$$f_H = c\sqrt{\frac{S_A}{lV}}. \quad (1)$$

where (to a first order) V is the volume of cavity 107, l is the length of the acoustic port 110 and $S_A$ is the area of the opening of the acoustic port 110. c is the speed of sound in the air in the acoustic port 110 and cavity 107.

It will be clear from equation 1 that the resonance frequency $f_H$ is proportional to the square root of the area $S_A$ of the acoustic port. If the area of the acoustic port 110 changes, for instance because the port becomes partly blocked, i.e. occluded, by some obstruction, the resonance frequency $f_H$ will change accordingly. In some embodiments therefore monitoring the frequency of the resonance peak that corresponds to the greatest magnitude of the signal component associated with the air resonance, i.e. the resonance frequency $f_H$, can be used to determine the blockage state of the acoustic port 110.

Figure 3:
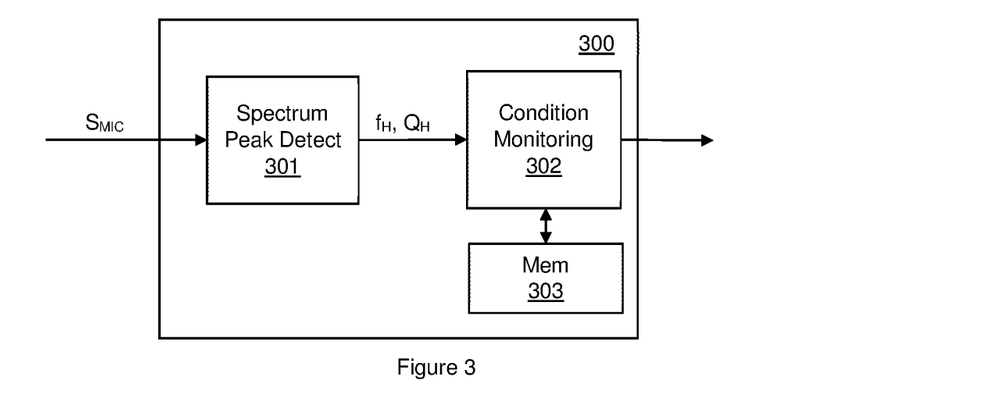
FIG. 3 illustrates a microphone monitoring apparatus for determining a blockage status and/or temperature condition.

In order to determine characteristic of this resonance peak, i.e. the resonance frequency $f_H$, from the microphone signal generated by a MEMS transducer, such as that shown in FIG. 1, microphone monitoring apparatus as shown in FIG. 3 may be used.

FIG. 3 illustrates a microphone monitoring apparatus 300 according to an embodiment which may be used for monitoring a microphone with an associated acoustic port 110, for instance such as the microphone arrangement illustrated in FIG. 1.

The microphone monitoring apparatus 300 is configured to receive microphone signals $S_{MIC}$ corresponding to the signals detected by the microphone transducer 101. As previously discussed, such a microphone signal contains a signal component corresponding to a resonance associated with acoustic port 110. Conveniently the microphone signal $S_{MIC}$ is a digital signal corresponding to the microphone output signal but in some embodiments an analogue microphone signal could be received and converted to a digital signal for further processing.

The microphone monitoring apparatus 300 comprises a spectrum peak detect block 301 for identifying a resonance peak associated with the acoustic port 110 in the microphone signal, i.e. an air resonance of the acoustic system. The spectrum peak detect block 301 is configured to determine one or more parameters related to the resonance peak and in the embodiment of FIG. 3 the spectral peak detect block 301 determines an indication of the resonance frequency $f_H$. In embodiments of the disclosure the spectrum peak detect block 301 also determines an indication of a quality factor $Q_H$ associated with the resonance peak as will be discussed in more detail below.

In some embodiments a condition monitoring block 302 is configured to compare the one or more parameters related to the resonance peak to one or more reference parameters, e.g. reference values of resonance frequency $f_H$ and quality factor $Q_H$, and to determine at least one operating condition for the microphone, for instance an indication of blockage status, i.e. whether acoustic port 110 is partly blocked, and/or an indication of air temperature or a change in air temperature.

As noted above with reference to equation (1) the resonance frequency $f_H$ of the resonance peak depends partly on the area and length of the acoustic port 110 and thus a partial blockage of the acoustic port would change the area of the port and/or the length of the acoustic port with a consequent variation in the resonance frequency $f_H$. However equation (1) also shows that the resonance frequency $f_H$ depends on the speed of sound c. The speed of sound c will itself vary with temperature of the air in the acoustic port 110 as will be understood by one skilled in the art. For an ideal gas the speed of sound varies with the square root of temperature. According to equation (1) above the Helmholtz frequency $f_H$ is proportional to the speed of sound c and hence will vary with the square root of temperature. As noted above the Helmholtz frequency $f_H$ is also proportional to the square root of acoustic port 110 area $S_A$. Thus, for a given microphone system if the opening of the acoustic port 110 were partly blocked, resulting in an effective reduction in the area of the acoustic port 110 of the order of 10% (with no change in air temperature), then a certain change in the resonance frequency $f_H$ would be expected. Equally however for the same microphone system if the acoustic port 110 were to remain unblocked, so there is no change in effective area, but the temperature decreased by 10% (as determined in Kelvin) then the same change in resonance frequency would be expected to result. If one were purely to look at the resonance frequency $f_H$ of the resonance peak 220 then it may not be possible to differentiate a change in frequency arising from the acoustic port 110 being partly blocked from a change in air temperature.

In embodiments of the present disclosure an indication of quality factor $Q_H$ of the resonance peak may also be determined. As will be well understood by one skilled in the art the quality factor $Q_H$ of a feature such as a resonance peak is an indication of the concentration or spread of energy of the resonance around the resonance frequency $f_H$, i.e. an indication of how wide or narrow the resonance peak is in terms of frequency. A higher quality factor $Q_H$ means that most of the energy of the resonance is concentrated at the resonance frequency $f_H$ and the signal magnitude due to the resonance drops off quickly for other frequencies. A lower quality factor $Q_H$ means that frequencies near the peak resonance frequency $f_H$ may also exhibit some relatively significant signal magnitude.

To a first order analysis the quality factor $Q_H$ of a microphone arrangement such as illustrated in FIG. 1 may be given by:

$$Q_H = 2\pi\sqrt{V\left(\frac{l}{S_A}\right)^3} \quad (2)$$

where V, l and $S_A$ are the cavity, i.e. chamber, volume, port length and port area respectively as defined above for equation 1.

It can thus be seen from equation (2) that the quality factor $Q_H$ of the resonance peak will vary with the area $S_A$ of the acoustic port 110 but the quality factor $Q_H$ is not temperature dependent. Thus a change in air temperature, without any change in acoustic port 110 area $S_A$, would be expected to result in a change in the resonance frequency $f_H$ of the resonance peak but without a corresponding change in the quality factor $Q_H$. However partial closure, i.e. blocking, of the acoustic port resulting in a change in port area $S_A$, without a change in air temperature, would be expected to result in a change in both the resonance frequency $f_H$ of the resonance peak and also the quality factor $Q_H$. Determining both the resonance frequency $f_H$ of the resonance peak, that is the frequency of the peak, and also the quality factor $Q_H$ thus allows for discrimination between changes in the resonance peak profile due to blockage in acoustic port 110 and changes due to temperature variation.

Figure 4:
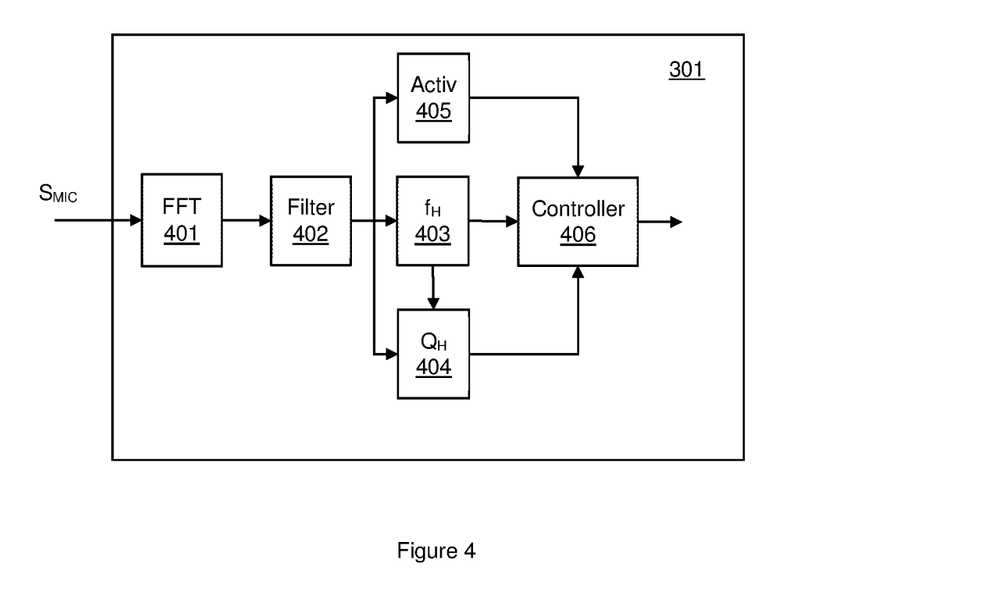
FIG. 4 illustrates an example of a resonance spectrum peak detect block.

FIG. 4 illustrates one example of the spectral peak detect block 301 according to an embodiment of the invention. In this example, the spectrum peak detect block 301 receives the microphone signal $S_{MIC}$ and a conversion block 401 converts the signal to a frequency domain version indicative of the signal magnitude, or power, for each frequency component, at least over a frequency range of interest, where any Helmholtz resonance may be expected. In this example a Fast Fourier Transform (FFT) block 401 generates an FFT of the microphone signal $S_{MIC}$, i.e. a spectrum signal indicative of the spectrum of the signals detected by the microphone transducer 101. The microphone signal may be windowed, i.e. bandpass filtered, over a frequency range of interest in producing the spectrum signal. The frequency range of interest, may for instance, be based on the expected Helmholtz resonance frequency, assuming an unblocked acoustic port at standard temperature and pressure, with some defined range, e.g. ±30%. In the example of FIG. 4 the output of the FFT 401 is filtered by filter block 402 to smooth the noise floor.

Other methods of determining a spectrum signal could be used however. For instance one alternative may use a filter bank. The microphone signal could be high-pass filtered to remove any low frequency components and the filtered signal processed by a filter bank, e.g. a bank of second-order resonators, to effectively sample the signal power at each of a number of defined frequencies/frequency bins within the frequency band of interest. In this example therefore FFT block 401 may be omitted and filter 402 may comprise a filter bank as described.

In any case a resonance frequency detection block 403 receives the spectrum signal and determines the resonance frequency of the resonance peak, i.e. the frequency that corresponds to the peak signal magnitude. There are various ways in which the resonance frequency of the resonance peak, i.e. $f_H$, may be determined.

For example in one embodiment the resonance frequency detection block 403 is configured to determine the maximum $A_{max}$ and minimum $A_{min}$ signal magnitude values of the spectrum signal within a frequency range of interest, e.g. between two defined frequency values $F_1$ and $F_2$. For instance, in one example the resonance frequency may be expected to fall within a frequency range between 12 kHz and 35 kHz and thus the resonance frequency detection may be applied over this frequency range.

Having identified the maximum $A_{max}$ and minimum $A_{min}$ values of the signal magnitude, i.e. a signal magnitude range, in the frequency range of interest, a first threshold $T_1$ may be determined above which it is expected substantially all of the relevant signal contribution is due to the resonance peak. The signal magnitude values above the first threshold $T_1$ may then be integrated across the frequency range from $F_1$ to $F_2$ to determine a total integral value and also the value of a first frequency $FR_1$ where the integral corresponds to half of the total value. At this first frequency $FR_1$, half of the total signal magnitude above the first threshold $T_1$ is at higher frequencies and half is at lower frequencies. Assuming that the resonance peak is largely evenly spread about the resonance frequency, e.g. the shape of the peak is reasonably symmetric, the value of the first frequency $FR_1$ thus corresponds to the resonance frequency $f_H$.

The first threshold $T_1$ should be high enough so that any signal magnitude above the first threshold is expected to be part of the resonance peak due to the acoustic port 110 resonance, but should be low enough to include a reasonable width of the resonance peak. A threshold of the order of 50-70%, say about 60% of the signal magnitude range between $A_{max}$ and $A_{min}$ may be used in some embodiments.

It will be appreciated however that other methods for finding the value of this resonance frequency $f_H$ associated with the acoustic port 110 may be used. For instance in some embodiments the resonance frequency $f_H$ may simply be assumed to be the frequency with the highest signal magnitude in the frequency range of interest.

In some embodiments the spectrum signal, or at least the values of the spectrum signal at certain defined frequencies/frequency bins, may be input to a suitably trained artificial neuron. The neuron may have been trained, for instance using FFT data and thresholds as described above.

Having determined a value for the peak frequency $f_H$, a quality factor determination block 404 may determine a quality factor $Q_H$ for the resonance peak. In some embodiments the quality factor block 404 may employ curve fitting to determine the quality factor $Q_H$. The quality factor block 404 may, for instance, be configured to determine a plurality of points associated with the resonance peak in the filtered spectrum signal and then fit a curve, e.g. a parabolic curve, to said points. A quality factor $Q_H$ can then be determined from the fitted curve.

In one example the quality factor determination block 404 may determine a first point corresponding to the peak of the resonance peak, i.e. the frequency and signal magnitude at the peak. The quality factor determination block 404 may then step a defined frequency interval either side of this first point and determine the relevant signal magnitudes for those frequencies to provide second and third points. The relevant frequency step may be chosen according to the particular implementation and may, for instance by determined partly by the resolution of the spectrum signal, e.g. the resolution of the FFT.

Figure 5:
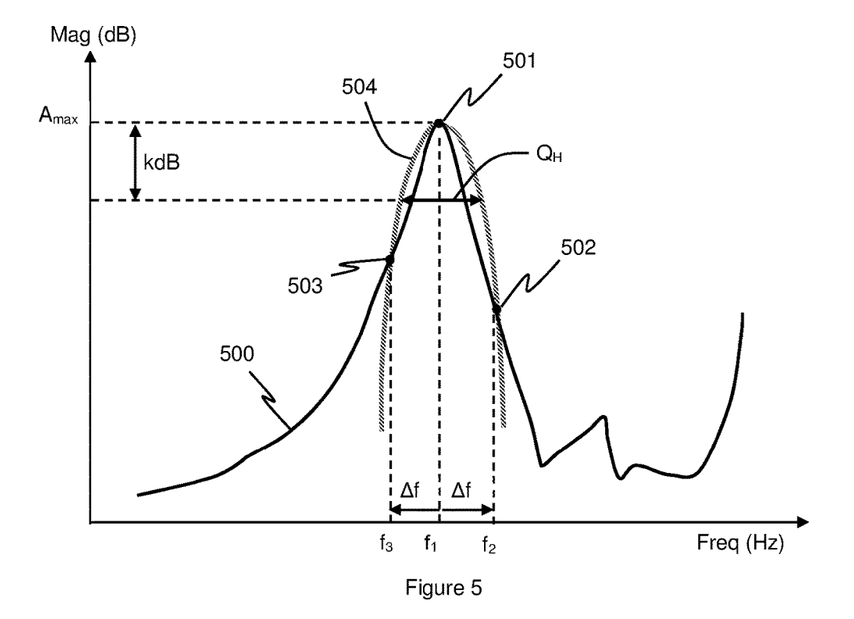
FIG. 5 illustrates the principles of determining a quality factor of a resonance peak according to one embodiment.

FIG. 5 illustrates an example of this approach. FIG. 5 illustrates an example spectrum signal 500 of signal magnitude against frequency over a frequency range of interest. A first point 501 is determined corresponding to the peak point of the resonance peak. In some embodiments the first point 501 may defined by determining the resonance frequency $f_H$ as described above and then determining the actual signal magnitude at this frequency $f_H$. In some embodiments however the first point 501 may be defined by looking for the frequency with the highest signal magnitude $A_{max}$. In which case, in some embodiments, the frequency that corresponds to the highest signal magnitude may be identified as the resonance frequency $f_H$ without applying the integration method described above.

In any event the frequency $f_1$ of this first point is determined. A second point 502 is defined by stepping up in frequency from $f_1$ by a defined amount $\Delta f$ and a third point is defined by stepping down in frequency from $f_1$ by the defined amount $\Delta f$ and in each case determining the relevant signal magnitude for those frequencies. Conveniently the same frequency interval $\Delta f$ is used to define the second and third points but this does not have to be the case and other frequency interval could be applied and taken into account when applying the subsequent curve fitting.

A parabolic curve 504 is then be defined which passes through all three points using any suitable known curve fitting process.

The quality factor determination block 501 then estimate the quality factor of the resonant peak, $Q_H$, as the width of the parabolic curve at a predetermined magnitude interval kdB below the maximum magnitude $A_{max}$. In some embodiments the predetermined magnitude interval kdB may be of the order of 3 dB.

Referring back to FIG. 4, the spectrum peak detect block 301 can thus determine values for both the resonance frequency $f_H$ and the quality factor $Q_H$ of the resonance peak. These values may be output from the spectrum peak detect block 301 to condition monitoring block 302 as illustrated in FIG. 3. However there may be some instances where it is not possible to determine accurate values for the resonance frequency $f_H$ and the quality factor $Q_H$ of the resonance peak. For instance if there is some significant external acoustic stimulus within the frequency band of interest there may be a signal component within the frequency band of interest that is not due to the resonance but which could interfere with measurement of the resonance peak.

In the example of FIG. 4 the spectrum peak detect block 301 thus has an activity detector 405 which is configured to monitor the filtered spectrum for any significant activity within the frequency band of interest for the Helmholtz resonance. On the timescale of operation of the spectrum peak detect block 301 the frequency profile of the resonance peak may not be expected to change much over time. Any temperature induced changes will tend to be gradual and if the acoustic port 110 becomes blocked the blockage may happen relatively suddenly but will likely remain in place for a period of time. However any external stimulus in the frequency band of interest may result in a continually changing spectral profile within the frequency band of interest.

In one example the activity detector 405 may thus compare the then current spectrum signal with a historic spectrum signal to determine the extent of any change in the relevant spectra. The activity detector 405 may thus receive the filtered FFT signal from filter 402 and may compare the current FFT signal to at least one stored previous FFT signal. For example the current FFT signal may be input to a buffer which stores a plurality of received FFT signals. The most recent FFT signal in the buffer may be subtracted term by term from the oldest FFT in the buffer, i.e. to determine any difference in signal magnitude at each frequency for the two FFTs. The absolute value of such difference may then be summed across the frequency range of interest to give an indication of activity in the frequency band of interest. If there is little activity in the frequency band of interest the signal magnitude at each frequency would not be expected to change much and thus the summed difference will be small. If however there is significant activity then some frequencies may exhibit significantly greater or lower signal magnitudes in the different FFTs and the summed activity value will be relatively high. An activity threshold $T_A$ may be applied to the determined sum, with data above the activity threshold $T_A$ being determined to be unreliable due to the level of activity in the frequency range. Any values of resonance frequency $f_H$ or quality factor $Q_H$ determined from a spectrum signal determined to be unreliable may be discarded.

Activity such as speech may not result in much signal power in the frequency range of interest for a Helmholtz resonance of a ported microphone, i.e. a microphone with an acoustic port 110, for instance in the example frequency range between 12 kHz and 35 kHz. Thus speech is unlikely to result in much activity in this frequency range of interest and the methods described above can typically be performed whilst the microphone is receiving speech. However the presence of an acoustic stimulus with energy in the frequency band of interest may result in a rapidly changing spectrum in that range with a result that the determined activity level exceeds the activity threshold $T_A$. Such data may therefore be discarded as being unreliable for detection of the parameters of the resonance peak associated with the acoustic port 110. The activity detector 405 may thus provide a control signal to a controller 406 indicating whether there is any significant activity in the frequency range of interest and hence whether the determined values of resonance frequency $f_H$ and quality factor $Q_H$ are likely to be reliable or not. In the event that the activity detector indicates that there was no significant activity the controller may output the resonance frequency $f_H$ and quality factor $Q_H$. In the event that the activity detector 405 does indicate that there was significant activity the controller 406 may not output any value or output the last previously reliable values.

The values of resonance frequency $f_H$ and quality factor $Q_H$ are output, when deemed reliable, to the condition monitoring block 302. The condition monitoring block 302 compares these parameters of the resonance peak to one or more reference parameter values. In some embodiments the reference values may correspond to a historically measured values, for instance one or more of the previously measured parameter values that may be stored as a reference value and/or a reference value could be determined as an average or some other combination of a plurality of previous values, i.e. historic values.

Comparing the values for the resonance frequency $f_H$ and quality factor $Q_H$ to one or more previously determined values will thus allow any significant change to be detected during the period of monitoring. In use, on power-on or reset of the microphone, the microphone may start producing a microphone output signal from which the input signal $S_{MIC}$ to the spectrum peak detect block 301 can be determined. In some embodiments the first values for resonance frequency $f_H$ and quality factor $Q_H$ to be determined may be used as initial reference values to which subsequently determined values may be compared. In some embodiments however at least one initial reference value may be retrieved from a memory 303 as an initial reference. This stored reference value could be based on a value stored by condition monitoring block 302 when the microphone was last operated. Thus the condition monitoring block 302 may be configured to store, in memory 303, values based on the determined resonance frequency $f_H$ or quality factor $Q_H$ to be used as reference values for a subsequent use of the microphone.

Additionally or alternatively at least one stored reference value may be a stored value of resonance frequency $f_H$ or quality factor $Q_H$ which corresponds to a known status or condition of the microphone operation. For example values of resonance frequency $f_H$ and/or quality factor $Q_H$ could be determined as part of an initial factory test, carried out at a controlled temperature, and stored permanently in the memory 303. Such a stored reference value may have been acquired in circumstances such that it is known that the acoustic port 110 is not blocked and such a stored reference value may thus be taken to correspond to an unblocked acoustic port 110 at a certain test temperature. In some embodiments at least one stored reference value may be a value which is modelled or calculated for the relevant microphone arrangement at certain conditions. In some embodiments there may be a plurality of calibrated reference values that correspond to measured, modelled or calculated values of resonance frequency $f_H$ and/or quality factor $Q_H$ for defined temperatures and/or defined partial blockage states of the acoustic port.

In some embodiments values for the resonance frequency $f_H$ and quality factor $Q_H$ may thus be determined substantially continuously in use when the microphone is providing an output signal, or periodically at certain regular or irregular time intervals to monitor for any significant change in the values by comparison to one or more reference values. In the event of any significant change the status block may determine the cause of the change.

There are at least three scenarios to consider when comparing the resonance frequency $f_H$ and the quality factor $Q_H$ to reference values.

In scenario 1 the resonance frequency $f_H$ and the quality factor $Q_H$ are both substantially the same as some reference values. If the relevant reference values are previously determined values then, in that case, it can be assumed that the profile of the resonance peak has not substantially changed since those reference values were determined. Thus it can be assumed that there is no significant change in the relevant dimensions of the acoustic port 110 contributing to the Helmholtz resonance and that there is no change in the blockage status of the acoustic port 110. If it is known or assumed that the reference values corresponds to the acoustic port 110 being unblocked then it can be determined that the acoustic port 110 remains unblocked. Further it can be determined that there has been no significant change in air temperature. If the relevant reference values correspond to a known temperature then it can be assumed that the air temperature corresponds to the known temperature.

In scenario 2 it is determined that the resonance frequency $f_H$ has changed from the reference value but the value of the quality factor $Q_H$ has not changed from the reference value. Given that the quality factor $Q_H$ is the same as the reference quality factor, and any change in acoustic port 110 dimensions would have resulted in a change in quality factor $Q_H$, it can thus be assumed that the blockage state of the acoustic port 110 is unchanged. If it is known or assumed that the reference value of quality factor corresponds to the acoustic port 110 being unblocked then it can be determined that the acoustic port 110 remains unblocked. The change of resonance frequency $f_H$ from the reference value in this scenario can thus be determined to arise from a change in air temperature.

In some embodiments, the condition monitoring block 302 may configured to simply determine that the air temperature has changed by determining a change in the resonance frequency $f_H$ that is not accompanied with a corresponding change in quality factor $Q_H$.

In some embodiments however the condition monitoring block may estimate the air temperature based on the determined value of resonance frequency $f_H$. As mentioned above if the quality factor $Q_H$ has not changed from a reference value known to correspond to an unblocked acoustic port 110, then all change in the value of resonance frequency $f_H$ may be attributed to a change in air temperature.

The temperature response for a particular microphone arrangement may be estimated, for instance according to:

$$f_H = 331.3 \sqrt{\left(\frac{\theta}{273.15} + 1\right)\frac{S_A}{lV}}, \quad \text{Eqn (3)}$$

where V, l and $S_A$ are the volume, length and port area of the ported microphone arrangement as discussed previously and $\theta$ is the temperature in degrees Celsius.

Thus the condition monitoring block may, in some embodiments be configured, in the event that the quality factor $Q_H$ is determined to correspond to a reference value indicative of an unblocked acoustic port 110, determine an estimate of air temperature based on the present value of the resonance frequency $f_H$.

The ability to determine an estimate of air temperature using a microphone in this way represents one novel aspect of this disclosure. An estimate of temperature may be useful in a number of applications.

In scenario 3, the resonance frequency $f_H$ is not the same as the reference value and the quality factor $Q_H$ of the resonant peak is also not the same as the reference quality factor. In such a case it can be determined that the blockage status of the acoustic port 110 has changed as the quality factor $Q_H$ is not the same as the reference quality factor. If it is known or assumed that the reference value corresponds to an unblocked acoustic port 110 then it may be assumed that the acoustic port 110 has become partly blocked, e.g. clogged. However, it may, in this case, not be clear whether the change in resonant peak is solely due to this blockage of the acoustic port 110, or whether there may also be a temperature factor contributing to the difference between the resonant peak and the reference peak.

In general however a blockage may occur relatively suddenly as the device with the microphone is placed onto a blocking object or vice versa or some debris enters the acoustic port 110. Temperature changes may be more gradual. Therefore if there is a relatively sudden change in quality factor associated with a relatively sudden change in resonance frequency then it may be determined that a blockage has occurred (or been removed).

Being able to detect that the acoustic port 110 is partly blocked is useful in a number of ways. A partly blocked acoustic port 110 may reduce the sensitivity of the microphone. If it is detected that an acoustic port 110 is blocked at least some aspect of the microphone operation or downstream processing may be adjusted to compensate or correct for the change in sensitivity. If the blocked state persists for some time an alert could be generated for the user of the device to check for any obstructions. Such an alert could, for example, be: an audible alert such as a bleep; a visual alert such as a warning message on the screen of the host device, such as a mobile phone for example; or a haptic alert such as a vibration of the host device or any combination of these three alerts.

Being able to determine a change in resonance frequency due to change in air temperature from a change in resonance frequency due to an acoustic port 110 blockage means that false alerts of blockage and unnecessary changes in operation of the microphone may be avoided.

It will be apparent from the discussion above that in order to detect a change in the blockage state of the acoustic port 110 associated with a microphone it would thus be sufficient to determine whether there is any change in quality factor $Q_H$ without needing to determine whether there is a change in resonance frequency. This represents a novel aspect of embodiments of the disclosure and thus in some embodiments the function of the resonance frequency determination block 403 may be omitted and embodiments may determine the quality factor only and monitor for any changes therein.

Equally in some embodiments the condition monitoring block 302 may receive indications of resonance frequency $f_H$ and quality factor $Q_H$ but may determine an estimate or temperature or temperature change only and may not report a separate blocked status (but may discount changes in resonance frequency $f_H$ due to blockage).

In other embodiments the condition monitoring block 302 may produce a status signal indicative of any change in blockage status and also indicative of a change in temperature and/or an estimate of the air temperature. The estimate of air temperature may be taken as an indication of ambient temperature.

Figure 6:
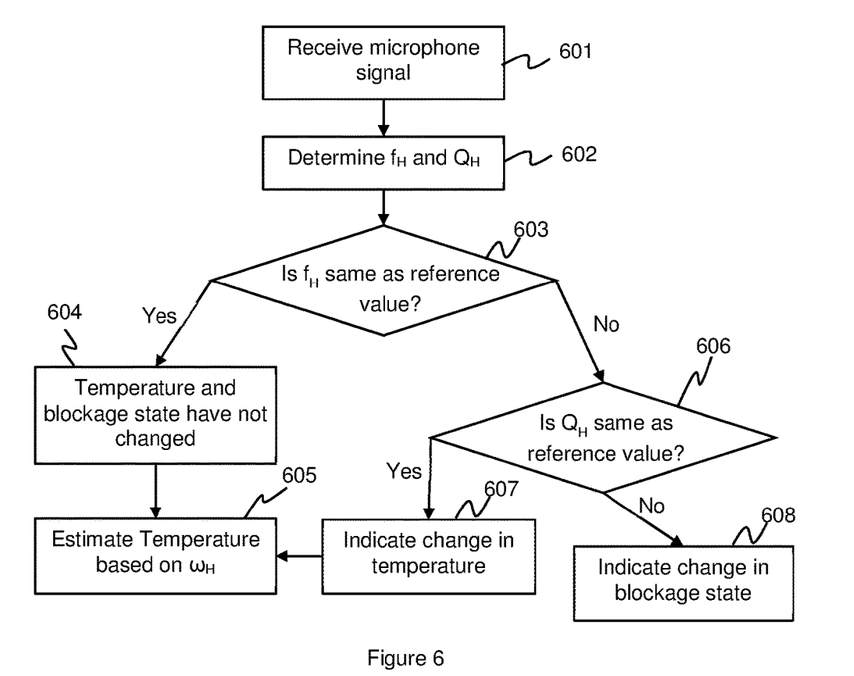
FIG. 6 illustrates a method of monitoring a microphone according to an embodiment.

FIG. 6 illustrates a method of monitoring a microphone according to the present invention.

In step 601 the method comprises receiving a microphone signal $S_{MIC}$ from the microphone. In step 602 the method comprises determining a resonance frequency $f_H$ associated with the acoustic port 110 in the microphone signal and also a quality factor $Q_H$ associated with the resonance peak. In step 603 it is determined if the resonance frequency is the same as a reference value. If the resonance frequency $f_H$ is the same as the reference value then it can be determined at step 604 that there is no change in temperature or blockage state from that corresponding to the reference value. In some embodiments the air temperature may thus be known based on the reference value or in some embodiments the air temperature may be estimated, in step 605, based on the determined resonance frequency.

If however at step 603 it is determines that that the resonant peak is not the same as the reference peak, the method passes to step 606 at which it is determined if the quality factor $Q_H$ has varied, e.g. from a reference value of quality factor.

If the quality factor $Q_H$ is the same as the reference value of quality factor then the method may indicate at step 607 that there has been a change in temperature. As discussed above the method may then determine an estimate of temperature based on the resonance frequency.

If however the quality factor $Q_H$ has changed from the reference value then it may be determined 608 that there has been some change in the blockage status of the acoustic port 110 associated with the microphone. If the reference quality factor corresponds to an unblocked port state then it may be signalled that the acoustic port 110 has become partly blocked.

Embodiments of the disclosure thus provide apparatus and methods for monitoring a microphone having an acoustic port 110. The methods and apparatus provide information on the air temperature of the microphone and/or on whether or not the acoustic port 110 of the microphone is blocked, by monitoring the frequency and quality factor of a resonance of the acoustic port 110 of the microphone.

Additionally or alternatively, in some embodiments the characterisation of the signal component due to resonance may be used in processing the output signal to reduce or mitigate the effect of noise in the microphone signal.

As mentioned above the resonance associated with the acoustic path from the environment of interest, e.g. the outside world, to the microphone transducer is an inherent resonance of the microphone structure and at least some signal component due to this resonance may be present whenever the microphone is receiving a signal of interest. The signal component due to resonance thus represents unwanted noise.

As discussed previously this resonance may, in some implementations, lie mainly outside the audio band. Thus this resonance has mainly been ignored for standard audio applications. However the effect of the resonance is that the transfer function between the pressure wave incident on the acoustic port 110 and the pressure experienced by the transducer 101 is non-linear with respect to frequency and high-frequency components are effectively amplified. The result is that acoustic signals in the near acoustic bandwidth may effectively be amplified, which in some instances may saturate the microphone. Also any acoustic noise is effectively amplified by the resonance decreasing the SNR performance.

Figure 7:
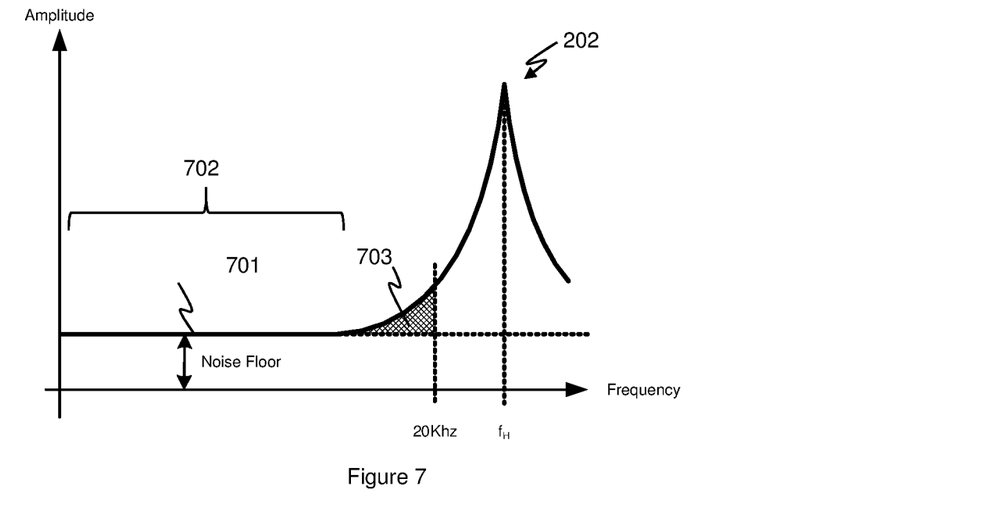
FIG. 7 illustrates an idealised plot of noise floor for a microphone device.

To illustrate this issue FIG. 7 illustrates an idealised plot of the signal response 701 from a microphone device, e.g. such as that illustrated in FIG. 1, in the absence of any specific acoustic stimulus. The microphone signal may, as discussed above, include a signal component due to the Helmholtz resonance, i.e. a resonance peak 202 centred on a resonance frequency $f_H$ as discussed previously. FIG. 7 illustrates an upper cutoff for the audio band at 20 kHz. As mentioned previously the resonance frequency $f_H$ may be outside of the audio band but the resonance peak itself may extend partly into the audio band.

Away from the resonance peak, in a first region indicated as 702, there may be a certain low signal level due to various other sources of noise. This represents the noise floor of the microphone system. Typically however the noise in this region 702 may be relatively flat with frequency and thus there may be a relatively consistent noise floor that does not vary substantially with frequency. The noise floor effectively increases at higher frequencies however due to the presence of the resonance. This results in a noise floor across the audio band that is not flat with frequency and the resonance effectively adds additional noise into the audio band as illustrated by shade region 703. As the resonance frequency tracks with temperature the noise floor in the audio band and the amount of additional noise will also vary with temperature.

In some embodiments of the disclosure, the microphone signal from the MEMS transducer may be analysed to determine an operating condition of the microphone, wherein the operating condition is an indication of the noise contribution due to the resonance. This may be an indication of the noise contribution within the signal band of interest for the signals from the microphone, e.g. an audio band, or the total contribution of the noise due to resonance. In some instances the microphone signal may be processed to reduce or eliminate such resonance components and thus improve the SNR (signal-to-noise ratio) of the microphone.

Figure 8:
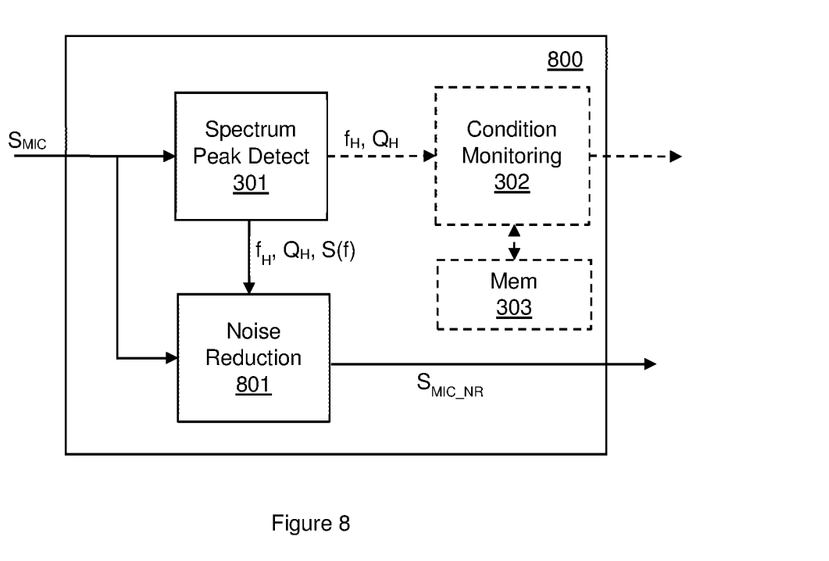
FIG. 8 illustrates a microphone monitoring apparatus for noise reduction.

FIG. 8 illustrates a microphone monitoring apparatus 800 according to an embodiment. The microphone monitoring apparatus receives a microphone signal $S_{MIC}$ derived from the microphone transducer in the same manner as discussed above. The microphone signal may be input to spectrum peak detect block 301 which may determine one or more characteristics of the resonance peak in the same manner as discussed above. The spectrum peak detect block 301 may output the determined characteristics to a noise reduction block which applies processing to the microphone signal $S_{MIC}$ to produce a processed version $S_{MIC\_NR}$ where at least some of the noise due to the resonance may be removed. In some instances the noise reduction block may comprise a filter or frequency processing block that is configured to effectively apply an inverse transfer function of amplitude to frequency to that determined for the resonance peak.

In some instances the spectrum peak detect block 301 may determine the resonance frequency $f_H$ and/or the quality factor $Q_H$ and supply such values to the noise reduction block to process the received microphone signal $S_{MIC}$ to produce the noise reduced microphone signal $S_{MIC\_NR}$. The noise reduction block may be configured to apply a certain transfer function or filter based on the indication of resonance frequency and/or the indication of quality factor. Additionally or alternative a spectrum signal S(f) indicative of the amplitude of the resonance contribution with frequency could be determined and supplied to the noise reduction block 801. The spectrum signal could, in some instance, comprise the parabolic curve determined by curve fitting by quality factor determination block 404 as discussed above in relation to FIG. 4. Additionally or alternatively the spectrum signal could be a signal derived from the output of filter 402 at times when the activity detector 405 indicates no substantial activity.

Figure 9:
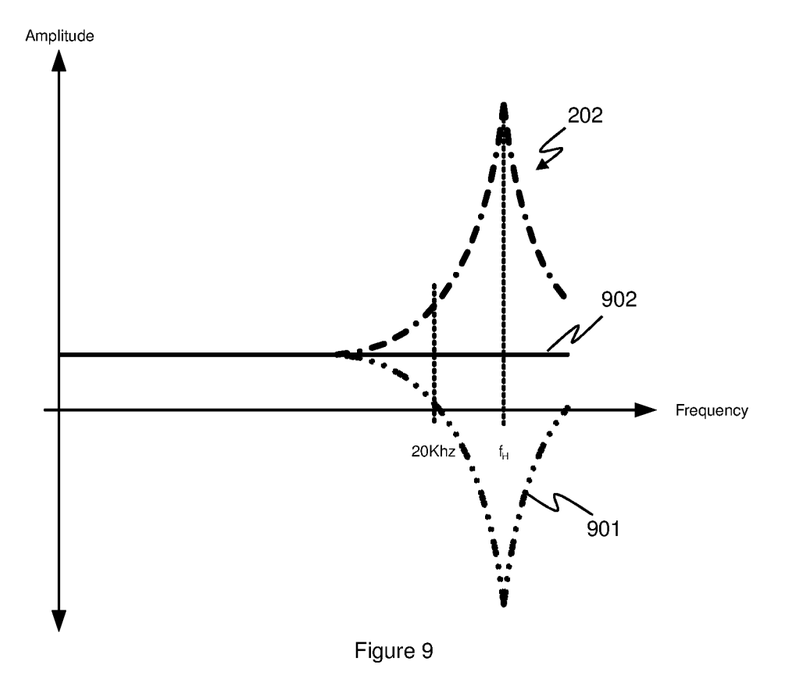
FIG. 9 illustrates an idealised plot of noise floor for the microphone monitoring apparatus of FIG. 8.

As mentioned above the noise reduction block may process the microphone signal $S_{MIC}$ to apply an inverse function to the determined variation of amplitude with frequency for the resonance peak. FIG. 9 illustrates that an inverse function 901 may be defined from the determined characteristic of the resonance peak 202. The inverse function 901 is applied to the microphone signal $S_{MIC}$ and at least partly compensates for the resonance effects. FIG. 9 illustrates that the resultant processed signal 902 is, in the absence of any specific acoustic stimulus, substantially flat across the whole frequency range. FIG. 9 shows an idealised inverse transfer function but even a non-ideal function can help reduce the effects of resonance noise and provide a generally flatter frequency response across a desired frequency band. FIG. 9 illustrates the inverse function being applied across substantially the whole frequency range of the resonance peak. It would however be possible to apply an inverse function only over a frequency band of interest, for example just over the audio band if higher frequencies are not of interest.

It should be noted that the microphone monitoring for noise reduction may be implemented with or without the monitoring discussed above to determine blockage status and/or a temperature condition. In at least some embodiments however the microphone monitoring apparatus may include noise reduction and a condition monitoring block for determining blockage status and/or temperature status and in such embodiments the spectrum peak detect block may be shared as illustrated in FIG. 8.

Embodiments are particularly applicable to monitoring of MEMS microphones. However the principles may be applied to sensing signals from other types of microphone, electret microphones for example. Embodiments may be arranged as part of an audio and/or signal processing circuit, for instance an audio circuit which may be provided in a host device. Embodiments of the invention also relate to MEMS transducer circuits. A circuit according to an embodiment of the present invention may be implemented as an integrated circuit. A MEMS transducer may form part of the integrated circuit on a monolithic substrate or be connected to the integrated circuit in use.

Embodiments may be implemented in a host device, especially a portable and/or battery powered host device such as a mobile telephone, an audio player, a video player, a PDA, a mobile computing platform such as a laptop computer or tablet and/or a games device for example.

Note that as used herein the term block shall be used to refer to a functional unit or functional module of an apparatus or device, i.e. apparatus for performing a particular function. A functional block may be implemented at least partly by dedicated hardware components such as custom defined circuitry or programmable logic gates or the like. Additionally or alternatively a functional block may at least partly be implemented by one or more software processors or appropriate code running on one or more suitable processors. A processor may be a dedicated processor for performing the function or may be a shared processor that may also be used to perform other tasks and in some instances may be general purpose processor or the like. Components of a functional block may be co-located on the same circuit and/or implemented by the same processor or at least some components forming part of a functional block may be remote from one another and may be implemented on different integrated circuits or run on different processors. At least some components or processes forming part of one block may be shared with another functional block. A functional block may itself comprise other modules or functional units. The term module shall be used be taken to have the same meaning as the term block.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

The invention claimed is:

1. An apparatus for monitoring for blockage of an acoustic port of a microphone, the apparatus comprising:
   a spectrum peak detect block for receiving a microphone signal and determining, from the microphone signal, a resonance frequency and a quality factor of a resonance associated with the acoustic port; and
   a condition monitoring block configured to determine any changes in resonance frequency and quality factor with respect to respective reference values of resonance frequency and quality factor and to determine a blockage status for the microphone based on said determined changes.

2. An apparatus as claimed in claim 1 wherein, if a change in quality factor with respect to one said reference value of quality factor is determined, the condition monitoring block is configured to output a status signal indicating that there has been a change in blockage status for the acoustic port from a blockage status that corresponds to that reference value of quality factor.

3. An apparatus as claimed in claim 1 wherein the condition monitoring block is configured such that at least one said reference value of quality factor is based one or more quality factors for the resonance associated with the acoustic port previously determined by the spectrum peak detect block.

4. An apparatus as claimed in claim 1 comprising a memory for storing a first reference value of quality factor known to correspond to an unblocked state of the acoustic port, wherein the condition monitoring block is configured, in use, to compare the determined quality factor to the stored first reference value and to determine that the acoustic port has become at least partly blocked if the determined quality factor is different to the first reference value of quality factor.

5. An apparatus as claimed in claim 1 wherein, if a change in resonance frequency without a change in quality factor is determined with respect to respective reference values of resonance frequency and quality factor, the condition monitoring block is configured to determine that the blockage status of the acoustic port has not changed.

6. An apparatus as claimed in claim 1 wherein, if a change in resonance frequency without a change in quality factor is determined with respect to respective reference values of resonance frequency and quality factor, the condition monitoring block is configured to output a status signal indicating that there has been a change in air temperature from a temperature that corresponds to said reference value of resonance frequency.

7. An apparatus as claimed in claim 6 wherein, in the event of determining a change in air temperature, the condition monitoring block is configured to determine an estimate of air temperature based on the determined resonance frequency.

8. An apparatus as claimed in claim 1 wherein, if no change in resonance frequency or quality factor is determined with respect to respective reference values of resonance frequency and quality factor, the condition monitoring block is configured to output a status signal indicating that there has been no change in operating condition from an operating condition that corresponds to said reference values.

9. An apparatus as claimed in claim 1 wherein the spectrum peak detect block comprises a conversion block configured to receive the microphone signal and output a spectrum signal corresponding to a frequency domain version of the microphone signal over at least a predefined frequency range.

10. An apparatus as claimed in claim 1 wherein the spectrum peak detect block comprises a filter bank configured to receive the microphone signal and output a spectrum signal comprising an indication of the signal amplitude at a plurality or frequencies or frequency bins over at least a predefined frequency range.

11. An apparatus as claimed in claim 9 wherein the spectrum peak detect block comprises a resonance frequency detection block configured to determine the resonance frequency from the spectrum signal.

12. An apparatus as claimed in claim 11 wherein the resonance frequency detection block is configured to identify a signal magnitude range between the highest and lowest signal magnitudes within the predefined frequency range, determine a first threshold within the identified signal range and integrate the values of signal magnitude above the first threshold across the predefined frequency range to identify a first frequency at which the integral equal half of the total integral and identify said first frequency as the resonance frequency.

13. An apparatus as claimed in claim 9 wherein the spectrum peak detect block comprises a quality factor determination block configured to determine said quality factor from the spectrum signal wherein the quality factor determination block is configured to determine a plurality of points associated with the resonance peak in the spectrum signal, to fit a curve to said determined points and to determine an indication of the quality factor from said curve.

14. An apparatus as claimed in claim 13 wherein the quality factor determination block is configured to determine the width of the fitted curve at a predetermined magnitude interval below the peak magnitude as the quality factor.

15. An apparatus as claimed in claim 9 further comprising an activity detector configured to determine an indication of activity within the predefined frequency range.

16. An apparatus as claimed in claim 15 wherein the spectrum peak detect block comprises a controller responsive to the activity detector, wherein the controller is configured such that if the activity is above an activity threshold the relevant spectrum signal is not used to determine an indication of resonance frequency or quality factor that is output from the spectrum peak detect block.

17. An apparatus as claimed in claim 1 comprising a noise reduction block configured to process the microphone signal based on at least one characteristic of said resonance associated with the acoustic port of the microphone so as to reduce noise in the processed microphone signal due to said resonance.

18. An electronic device comprising an apparatus as claimed in claim 1 wherein the apparatus is at least one of a: portable device; a battery powered device; a communications device; a mobile or cellular telephone; a smartphone device; a computing device; a laptop, notebook or tablet computer; a gaming device; a wearable device; a voice-controlled or voice activated device.

19. An apparatus for monitoring for blockage of an acoustic port of a microphone, the apparatus comprising:
 a spectrum peak detect module configured to analyse a received microphone signal to determine a resonance frequency and a quality factor of a resonance associated with the acoustic port; and
 a condition monitoring block configured to determine a blockage status for the acoustic port of the microphone based on both said determined resonance frequency and said determined quality factor.

20. An apparatus for monitoring for blockage of an acoustic port of a microphone, the apparatus comprising:
 a quality factor determining block for receiving a microphone signal and determining, from the microphone signal, a quality factor associated of a resonance associated with the acoustic port; and,
 a condition monitoring block configured determine a blockage status for the acoustic port of the microphone based on said determined quality factor.

* * * * *

UNITED STATES PATENT AND TRADEMARK OFFICE
CERTIFICATE OF CORRECTION

PATENT NO. : 10,237,668 B2
APPLICATION NO. : 15/935542
DATED : March 19, 2019
INVENTOR(S) : Lesso et al.

Page 1 of 2

It is certified that error appears in the above-identified patent and that said Letters Patent is hereby corrected as shown below:

In the Drawings

In Fig. 6, Sheet 3 of 5, for Step "605", in Line 2, delete "$\omega_H$" and insert -- $f_H$ --, therefor.

In the Specification

Column 1, Line 6, delete "to determining" and insert -- to determine --, therefor.

Column 2, Line 43, delete "plurality or frequencies" and insert -- plurality of frequencies --, therefor.

Column 2, Line 44, delete "range" and insert -- range. --, therefor.

Column 2, Lines 62-63, delete "additionally or alternative" and insert -- additionally or alternatively --, therefor.

Column 4, Line 23, delete "configured determine" and insert -- configured to determine --, therefor.

Column 4, Lines 23-24, delete "an blockage" and insert -- a blockage --, therefor.

Column 5, Line 30, delete "interest" and insert -- interest. --, therefor.

Column 5, Line 57, delete "DESCRIPTION" and insert -- DETAILED DESCRIPTION --, therefor.

Column 7, Line 8, delete "at a least" and insert -- at least --, therefor.

Column 7, Line 28, delete "substrate 101" and insert -- substrate 102 --, therefor.

Column 9, Line 16, delete "107, I and" and insert -- 107, 1 and --, therefor.

Column 10, Line 58, delete "V, I and" and insert -- V, 1 and --, therefor.

Signed and Sealed this
Twenty-eighth Day of May, 2019

Andrei Iancu
*Director of the United States Patent and Trademark Office*

CERTIFICATE OF CORRECTION (continued)
U.S. Pat. No. 10,237,668 B2

Column 12, Line 41, delete "instance by" and insert -- instance be --, therefor.

Column 12, Line 49, delete "may defined" and insert -- may be defined --, therefor.

Column 15, Line 49, delete "may configured" and insert -- may be configured --, therefor.

Column 16, Line 1, delete "V, I and" and insert -- V, l and --, therefor.

Column 17, Line 26, delete "determines that that" and insert -- determined that --, therefor.

Column 19, Line 2, delete "Additionally or alternative" and insert -- Additionally or alternatively --, therefor.

In the Claims

Column 21, Line 24, Claim 10 should read:
10. An apparatus as claimed in claim 1 wherein the spectrum peak detect block comprises a filter bank configured to receive the microphone signal and output a spectrum signal comprising an indication of the signal amplitude at a plurality of frequencies or frequency bins over at least a predefined frequency range.

Column 22, Line 39, Claim 20 should read:
20. An apparatus for monitoring for blockage of an acoustic port of a microphone, the apparatus comprising: a quality factor determining block for receiving a microphone signal and determining, from the microphone signal, a quality factor associated of a resonance associated with the acoustic port; and a condition monitoring block configured to determine a blockage status for the acoustic port of the microphone based on said determined quality factor.